United States Patent [19]  [11]  4,315,935
Ali  [45]  Feb. 16, 1982

[54] N,N'-BIS[SUBSTITUTED-1,2,3,4-TETRAHYDROISOQUINOLINOLYL]DISULFONYLIMIDES AND ANTIALLERGIC COMPOSITIONS AND METHOD OF USE

[75] Inventor: Fadia E. Ali, Cherry Hill, N.J.

[73] Assignee: SmithKline Corporation, Philadelphia, Pa.

[21] Appl. No.: 159,340

[22] Filed: Jun. 13, 1980

Related U.S. Application Data

[63] Continuation-in-part of Ser. No. 140,021, Apr. 14, 1980, abandoned.

[51] Int. Cl.$^3$ .................... A61K 31/47; C07D 217/16
[52] U.S. Cl. .................................... 424/258; 546/139; 546/140; 546/146
[58] Field of Search .................... 546/140; 424/258

[56] References Cited

U.S. PATENT DOCUMENTS 3,882,148  5/1975  Augstein et al. .................... 424/283
4,179,507  12/1979  Stenlake et al. .................... 546/140
4,192,877  3/1980  Savarese et al. .................... 546/140
4,252,818  2/1981  Rokach et al. .................... 424/283

OTHER PUBLICATIONS

"Chem. Eng. News", May 11, 1970, pp. 103–104.
Appleton et al., "J. Med. Chem.", vol. 20, 1970, pp. 371–379.
Chand, "Agents and Action", vol. 912, 1979, pp. 133–140.

Primary Examiner—Donald G. Daus
Assistant Examiner—James H. Turnipseed
Attorney, Agent, or Firm—Joseph F. DiPrima; Richard D. Foggio; Alan D. Lourie

[57] ABSTRACT

Imidodisulfamide derivatives useful in the treatment of allergic conditions are prepared by reaction of an appropriately substituted tetrahydroisoquinoline and bis(chlorosulfonyl)imide in the presence of a tertiary amine.

25 Claims, No Drawings

N,N'-BIS[SUBSTITUTED-1,2,3,4-TETRAHYDROISOQUINOLINOLYL]DISULFONYLIMIDES AND ANTIALLERGIC COMPOSITIONS AND METHOD OF USE

This is a continuation-in-part of application Ser. No. 140,021, filed on Apr. 14, 1980 now abandoned.

This invention relates to novel imidodisulfamides which are useful as end-organ antagonists of slow reacting substance of anaphylaxis. This substance (SRS-A) has been suggested to be an important mediator of anaphylaxis in human asthma. By antagonizing the effects of this or other pharmacologically active mediators at the end-organ, bronchial smooth muscle, the compounds of this invention are valuable in the treatment of allergic diseases such as asthma.

The imidodisulfamide compounds of this invention are represented by the following general structural formula (I):

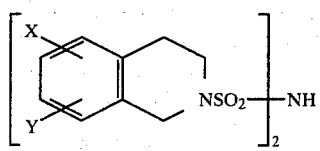

wherein X is hydrogen, methyl, bromo or chloro; and Y is a benzeneaminosulfonyl radical of the formula:

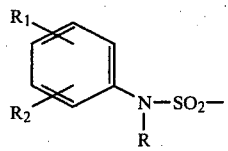

wherein R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl, and when $R_2$ is methyl, $R_1$ is methyl; or an alkali metal salt of said compounds.

The compounds of the formula (I) are conveniently prepared as shown in the following scheme:

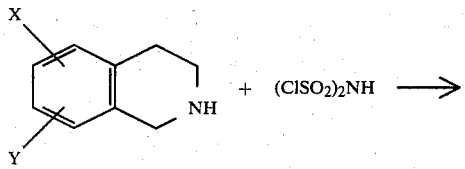

in which X and Y are described above. Thus, the appropriately substituted tetrahydroisoquinoline is reacted with bis(chlorosulfonyl)imide in the presence of a nonnucleophilic base, for example triethylamine or pyridine, and in an inert organic solvent, for example acetonitrile, at a temperature which is first below 0° C. and then at from about 0° C. to ambient temperature for at least 12 hours. Treatment of the reaction product with dilute mineral acid affords the imidodisulfamide compound.

Alkali metal salts of the compounds of the formula (I), for example, the sodium or potassium salts, are obtainable by treatment of the compounds with the appropriate metal alkoxide, for example methoxide, in an alkanol solvent such as methanol; by treatment of the compounds with an alkali metal hydride, such as sodium hydride or potassium hydride, in a polar non-protic solvent, such as tetrahydrofuran, or dimethoxyethane; or by treatment of the compounds with a cationic exchange resin, such as a sulfonic acid resin in the sodium form.

Illustrative of the instant invention wherein the tetrahydroisoquinoline moiety is substituted in the 7-position with the benzeneaminosulfonyl radical are compounds of the formula (II).

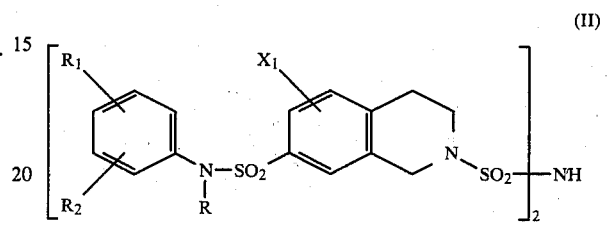

wherein $X_1$ is hydrogen, methyl, bromo or chloro; R represents hydrogen or methyl; $R_1$ represents hydrogen, bromo, chloro, nitro, methyl, trifluoromethyl or methoxy; and $R_2$ represents hydrogen, chloro or methyl provided that when $R_2$ is chloro, $R_1$ is chloro, methyl or trifluoromethyl and when $R_2$ is methyl, $R_1$ is methyl or an alkali metal salt of the compounds of the formula (II).

Particular compounds of the instant invention are the compounds of formula (II) wherein $X_1$ is hydrogen.

Specific compounds of the instant invention when $X_1$ is hydrogen are the compounds of the formula (II) wherein:

(a) R and $R_2$ both represent hydrogen and $R_1$ represents hydrogen; 3- or 4-bromo; 2-, 3- or 4-chloro; 3-nitro; 3- or 4-trifluoromethyl; or 4-methoxy;

(b) R represents hydrogen; $R_2$ represents 3-chloro and $R_1$ represents 4-chloro or 4-methyl;

(c) R represents hydrogen; $R_2$ represents 4-chloro; and $R_1$ represents 3-trifluoromethyl;

(d) R represents hydrogen; $R_2$ represents 3-methyl; and $R_1$ represents 4-methyl; and (e) R represents methyl; $R_2$ represents hydrogen; and $R_1$ represents 4-chloro.

More specifically, compounds included in the instant invention are of the formula (II) wherein $X_1$, R and $R_2$ represent hydrogen, and $R_1$ represents 3-chloro or 3-bromo and wherein $X_1$ and R represent hydrogen, $R_2$ represents 3-methyl and $R_1$ represents 4-methyl.

The compounds of the formula (II) are conveniently prepared as shown in the following scheme.

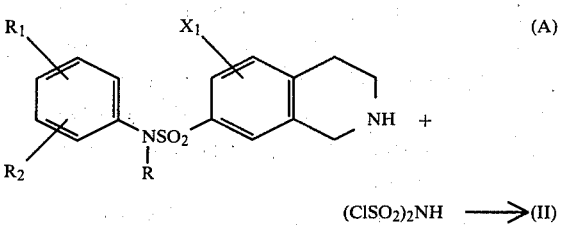

in which $X_1$, R, $R_1$ and $R_2$ are described above.

The starting substituted tetrahydroisoquinoline (A) may be prepared from chlorosulfonyl tetrahydroisoquinoline (B) via the following synthetic pathway:

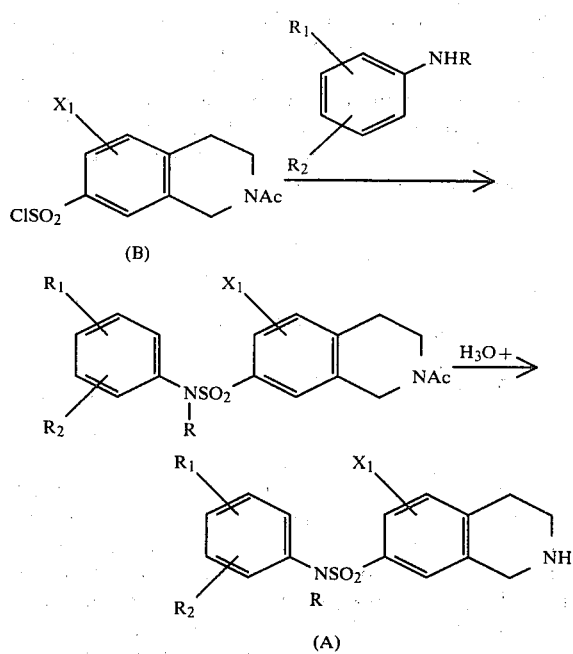

The compound (B) is reacted with the appropriately substituted aniline followed by treatment with dilute mineral acid to give the appropriately substituted tetrahydroisoquinoline (A). Bis(chlorosulfonyl)imide is prepared from chlorosulfonic acid and chlorosulfonylisocyanate.

Chlorosulfonyltetrahydroisoquinoline (B) wherein $X_1$ is 5-methyl, 5-bromo or 5-chloro may be prepared via a multistep synthesis starting from methyl acrylate and the appropriately substituted anisidine as described hereinafter.

Chlorosulfonyltetrahydroisoquinoline (B) wherein $X_1$ is hydrogen, 6-methyl, 6-bromo or 6-chloro may be prepared by treating the appropriately substituted 2-acetyl-tetrahydroisoquinoline with chlorosulfonic acid.

Chlorosulfonyltetrahydroisoquinoline (B) wherein $X_1$ is 8-chloro or 8-bromo may be prepared by halogenating 7-methoxyisoquinoline with either chlorine or bromine followed by the conversion of the methoxy group into a mercapto group as described hereinafter. The mercaptoisoquinoline is then partially hydrogenated to the corresponding tetrahydroisoquinoline which is converted to the chlorosulfonyl derivative by known procedures.

Illustrative of the instant invention wherein the tetrahydroisoquinoline moiety is substituted in the 6-position with a benzeneaminosulfonyl group are compounds of the formula (III).

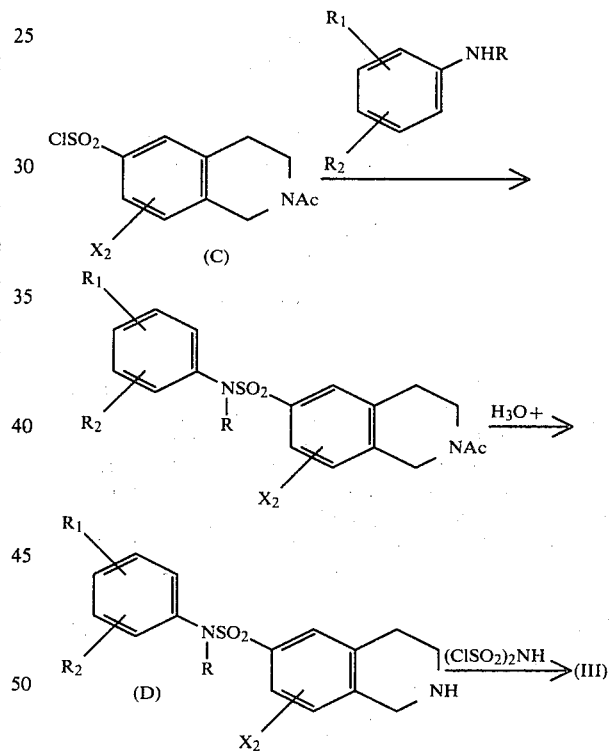

wherein $X_2$ is methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt of said compounds.

The compounds of formula (III) are conveniently prepared as shown in the following scheme.

The chlorosulfonyltetrahydroisoquinoline (C) is converted into compounds of the formula (III) by reacting compound (C) with the appropriately substituted aniline followed by hydrolysis to give compound (D) which is then coupled with bis(chlorosulfonyl)imide.

Chlorosulfonyltetrahydroisoquinoline (C) wherein $X_2$ is 5-methyl, 5-bromo or 5-chloro may be prepared via a multistep synthesis starting from the appropriately substituted 3-haloaniline and methyl acrylate to the corresponding 6-halotetrahydroisoquinoline which is converted into compound (C) through a mercapto intermediate.

Chlorosulfonyltetrahydroisoquinoline (C) wherein $X_2$ is 7-methyl, 7-bromo or 7-chloro may be prepared by the chlorosulfonation of the appropriately substituted tetrahydroisoquinoline at ambient temperature.

Chlorosulfonyltetrahydroisoquinoline (C) wherein $X_2$ is 8-methyl, 8-bromo or 8-chloro may be prepared via a multistep synthesis starting with the appropriate substituted p-anisaldehyde and 2,2-di-lower-alkoxyethylamine by the Pomeranz-Fritsch reaction to an appropriately substituted 6-methoxyisoquinoline which after the conversion of the methoxy group to a mercapto group is hydrogenated to the appropriately substituted mercapto tetrahydroisoquinoline, which is then converted to the compound (C) by known procedures.

Illustrative of the instant invention wherein the tetrahydroisoquinoline moiety is substituted in the 8-position with a benzeneaminosulfonyl group are compounds of the formula (IV)

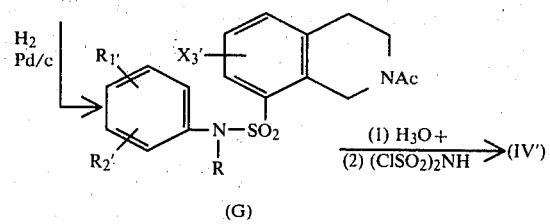

wherein $X_3$ is hydrogen, methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt thereof.

A particular compound of the instant invention of the formula (IV) is the compound wherein $X_3$ is 7-chloro; R and $R_2$ are each hydrogen; and $R_1$ is 3-chloro.

The compounds of the formla (IV) are conveniently prepared as shown in the following scheme.

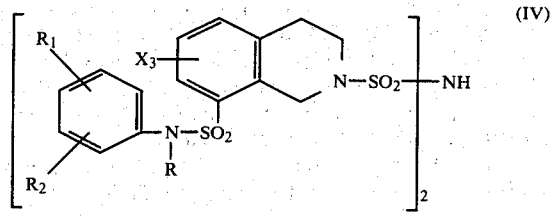

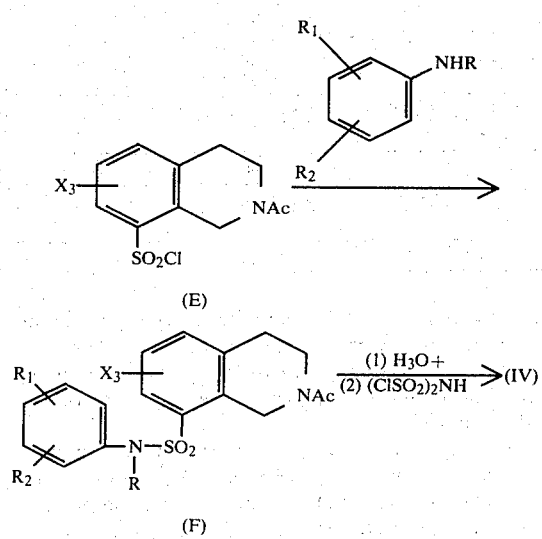

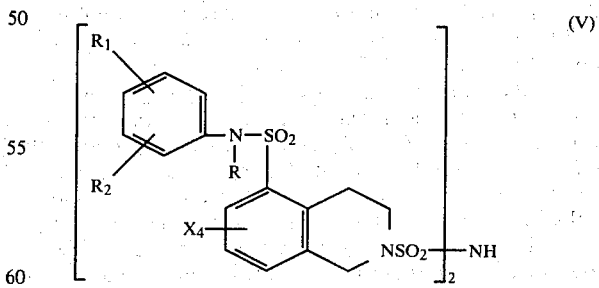

The chlorosulfonyl compound (E) is reacted with the appropriately substituted aniline to afford compound (F) which, after hydrolysis of the 2-acetyl group, is reacted with bis(chlorosulfonyl)imide to yield compounds of the formula (IV). Compound (F) may also be hydrogenated to afford the deshalo compounds (G) wherein $X_3'$, $R_1'$ and $R_2'$ are the same as $X_3$, $R_1$ and $R_2$ respectively but are not bromo or chloro. Compound (G) is then coupled with bis(chlorosulfonyl)imide to afford the deshalo compounds of the formula (IV), designated above as (IV'). It should be noted that the deshalo analogs of the compounds (II), (III) and (V) may also be prepared by the hydrogenolysis of the appropriate 2-acetyl-benzeneaminosulfonyltetrahydroisoquinoline.

Chlorosulfonyltetrahydroisoquinoline (E) wherein $X_3$ is 5-bromo or 5-chloro may be prepared from 5-amino-isoquinoline by converting the amino group to either a bromo or chloro group followed by hydrogenation and chlorosulfonation.

Chlorosulfonyltetrahydroisoquinoline (E) wherein $X_3$ is 6-methyl, 6-bromo or 6-chloro may be prepared via a multistep synthesis starting with the appropriately substituted o-anisaldehyde employing the Pomeranz-Fritsch reaction as discussed above.

Chlorosulfonyltetrahydroisoquinoline (E) wherein $X_3$ is 7-methyl, 7-bromo or 7-chloro may be prepared from the appropriately substituted 8-halotetrahydroisoquinoline which is converted to a 8-mercaptotetrahydroisoquinoline with benzylmercaptan and sodium hydride. The mercapto group is then converted to the chlorosulfonyl group via known methods.

Illustrative of the instant invention wherein the tetrahydroisoquinoline moiety is substituted in the 5-position with a benzeneaminosulfonyl group are compounds of the formula (V)

wherein $X_4$ is methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt of said compounds.

A particular compound of the instant invention is a compound of the formula (V) wherein $X_4$ is 8-chloro; R and $R_2$ are each hydrogen; and $R_1$ is 3-chloro.

The compounds of the formula (V) are conveniently prepared as shown in the following scheme.

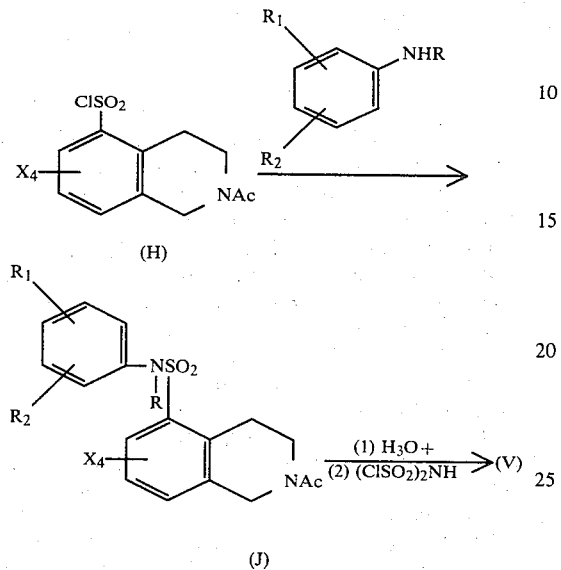

Following analogous procedures, for the preparation of the compounds of the formula (II) the chlorosulfonyl compound (H) is converted into the compounds of the formula (V).

Chlorosulfonyltetrahydroisoquinoline (H) wherein $X_4$ is 6-methyl, 6-bromo or 6-chloro may be prepared via a multistep synthesis starting with the appropriately substituted o-anisidine and methyl acrylate as described hereinafter. An alternate synthesis of this compound may be accomplished by nitrating the appropriately substituted tetrahydroisoquinoline followed by the reduction of the resultant 5-nitrotetrahydroisoquinoline to the amino derivative, which is converted to the chlorosulfonyl group employing known reactions.

Chlorosulfonyltetrahydroisoquinoline (H) wherein $X_4$ is 7-methyl, 7-bromo or 7-chloro may be prepared from the appropriately substituted o-anisaldehyde and methylacrylate as described hereinafter.

Chlorosulfonyltetrahydroisoquinoline (H) wherein $X_4$ is 8-methyl, 8-bromo or 8-chloro may be prepared by chlorosulfonating the appropriately substituted tetrahydroisoquinoline with chlorosulfonic acid at low temperature, for example $-70°$ C.

The SRS-A antagonist activity of the compounds of this invention is measured by the ability of the active medicament to inhibit SRS-A induced contraction of guinea pig ileum. In this test system, sections of ileum are resected from guinea pigs and placed in 5 ml. tissue baths containing a modified Tyrode's solution. One end of the tissue is fixed to a glass tissue holder, the other is connected to a force-displacement transducer and the tissue is placed under a tension of 500 mg. Isometric tissue contractions are recorded on a six channel polygraph. Baths are constantly aerated with 95% $O_2$-5% $CO_2$. After a 20 minute stabilization period a concentration of the appropriate agonist which provides a contraction height of 60-80% of the maximum obtainable to that agonist (as determined from full sequential concentration—response curves in separate experiments) is added to the tissue bath and the response recorded. The procedure is repeated until reproducible responses are obtained. For most agonists, two applications in rapid succession, followed 15 minutes later by a third, is sufficient to establish reproducibility. Experimental tissues are incubated with the selected concentration of the test compounds for 15 minutes. Experimental and control tissues are subjected to 5 bath changes during the incubation interval. Changes in bath fluid during the incubation period are helpful in insuring the reproducibility of tissue responses to the agonist. The same concentration of the agonist is reapplied in the presence of the test compound and the response registered and compared with controls. Percent inhibition produced by the test compound is calculated by substracting the mean percentage change in control tissue from the means percentage change in tissues exposed to the test compound. Additional compounds are then evaluated as long as the tissue remains reproducibly responsive to the agonist. Six tissues obtained from 6 animals are used simultaneously—3 controls and 3 experimental.

The compounds of this invention tested at concentrations of from $5 \times 10^{-5}$ M to $1 \times 10^{-6}$ M produce marked antagonism of partially purified slow reacting substance of anaphylaxis obtained from guinea pig lung. The agonist is employed at a concentration of 40 μg/ml. Representative of this effect, tabulated below are a number of the claimed compounds and percentage antagonism of SRS-A at various compound concentrations.

| COMPOUNDS OF THE FORMULA (II) | | | | | |
|---|---|---|---|---|---|
| R | $R_1$ | $R_2$ | $X_1$ | COMPOUND CONCENTRATION (M) | PERCENTAGE ANTAGONISM |
| H | 3-Cl | H | H | $5 \times 10^{-6}$ | 67.5 |
| H | H | H | H | $5 \times 10^{-6}$ | 42.3 |
| H | 2-Cl | H | H | $5 \times 10^{-6}$ | 24.8 |
| H | 4-Cl | H | H | $5 \times 10^{-6}$ | 51.2 |
| H | 3-Br | H | H | $5 \times 10^{-6}$ | 68.0 |
| H | 3-Br | H | H | $1 \times 10^{-6}$ | 54.0 |
| H | 4-Br | H | H | $5 \times 10^{-6}$ | 42.2 |
| H | 3-$NO_2$ | H | H | $5 \times 10^{-6}$ | 36.0 |
| H | 3-$CF_3$ | H | H | $5 \times 10^{-6}$ | 65.0 |
| H | 4-$CF_3$ | H | H | $5 \times 10^{-6}$ | 57.0 |
| H | 4-$CF_3$ | H | H | $1 \times 10^{-6}$ | 49.0 |
| H | 4-Cl | 3-Cl | H | $5 \times 10^{-6}$ | 56.0 |
| H | 4-Cl | 3-Cl | H | $1 \times 10^{-6}$ | 49.0 |
| H | 3-$CF_3$ | 4-Cl | H | $5 \times 10^{-6}$ | 91.5 |
| H | 3-$CF_3$ | 4-Cl | H | $1 \times 10^{-6}$ | 41.0 |
| H | 4-$CH_3$ | 3-$CH_3$ | H | $5 \times 10^{-6}$ | 62.0 |
| H | 4-$CH_3$ | 3-Cl | H | $5 \times 10^{-6}$ | 84.0 |
| $CH_3$ | 4-Cl | H | H | $5 \times 10^{-6}$ | 57.3 |
| COMPOUNDS OF THE FORMULA (IV) | | | | | |
| R | $R_1$ | $R_2$ | $X_3$ | | |
| H | 3-Cl | H | 7-Cl | $5 \times 10^{-6}$ | 48.0 |
| COMPOUNDS OF THE FORMULA (V) | | | | | |
| R | $R_1$ | $R_2$ | $X_4$ | | |
| H | 3-Cl | H | 8-Cl | $5 \times 10^{-6}$ | 63.0 |

The specificity of the antagonist activity of the compounds of this invention is demonstrated by relatively low levels of antagonism toward agonists such as potassium chloride, serotonin, histamine and the prostaglandins $F_{2\alpha}$ and $E_2$.

The compounds of this invention may be administered in conventional pharmaceutical compositions comprising an appropriate amount of a compound of formula I in association with a pharmaceutical carrier or diluent. The nature of the composition and the pharmaceutical carrier or diluent will of course depend upon the intended route of administration, i.e. parenterally or by inhalation. Usually a compound is administered to an animal or human subject in a composition comprising an amount sufficient to produce an inhibition of the symptoms of an allergic response. When employed in this manner, the dosage of the composition is such that from 0.5 mg. to 500 mg. of active ingredient are administered at each administration. For convenience equal doses will be administered 1 to 4 times daily with the daily dosage regimen being selected from about 0.5 mg. to about 2000 mg.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant such as dichlorodifluoromethane or chlorotrifluoroethane to be administered from a pressurized container. The compositions may also comprise the solid active ingredient diluted with a solid diluent, e.g. lactose, for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension. Exemplary of liquid carriers are peanut oil, olive oil or water.

The pharmaceutical preparations thus described are made following the conventional techniques of the pharmaceutical chemist as appropriate to the desired end product.

Included within the scope of this invention is the method of inhibiting the symptoms of an allergic response resulting from a mediator release which comprises administering to an animal or human subject a therapeutically effective amount for producing said inhibition of a compound of formula I, preferably in the form of a pharmaceutical composition. The administration may be carried out in dosage units at suitable intervals or in single doses as needed. Usually the method of this invention will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

Preparation of Bis(chlorosulfonyl)imide

A mixture of 166 g. (1.42 mole) of chlorosulfonic acid and 202 g. (1.42 mole) of chlorosulfonylisocyanate was heated under reflux (110° C.) in an oil bath until the evolution of carbon dioxide ceased. The crude product was distilled in vacuo to yield bis(chlorosulfonyl)imide, b.p. (1.5 mm.) 100° C.

Preparation of 2-Acetyl-1,2,3,4-Tetrahydroisoquinoline

A mixture of 100 g. (0.75 mole) 1,2,3,4-tetrahydroisoquinoline and 150 ml. acetic anhydride was stirred at ambient temperature for 24 hours and then concentrated to dryness at reduced pressure. The residual liquid was dissolved in methylene chloride and solid potassium carbonate was added to neutralize the solution. The excess potassium carbonate was removed by filtration and the filtrate was concentrated to dryness at reduced pressure to afford 2-acetyl-1,2,3,4-tetrahydroisoquinoline as a yellow liquid.

Preparation of 2-Acetyl-7-Chlorosulfonyl-1,2,3,4,-Tetrahydroisoquinoline

To a solution of 140 g. (0.8 mole) 2-acetyl-1,2,3,4-tetrahydroisoquinoline in 150 ml. dry methylene chloride at −15° C. with sufficient stirring was added dropwise 300 ml. (4.5 mole) chlorosulfonic acid. After the addition of the chlorosulfonic acid was complete, the reaction mixture was stirred for one hour at −15° C. and then heated to reflux for 2 hours. The reaction mixture was then cooled to 10° C. and then cautiously poured onto 3 l. of ice. The crude reaction product was then extracted in methylene chloride (2×150 ml.), dried over anhydrous magnesium sulfate and filtered. The filtrate was concentrated to dryness at reduced pressure to afford 2-acetyl-7-chlorosulfonyl-1,2,3,4,-tetrahydroisoquinoline as a viscous yellow oil.

Preparation of 2-Acetyl-7-(3-Chlorobenzeneaminosulfonyl)-1,2,3,4-Tetrahydroisoquinoline A mixture of 102 g. (0.37 mole) 2-acetyl-7-chlorosulfonyl-1,2,3,4,-tetrahydroisoquinoline, 47.6 g. (0.37 mole) 3-chloroaniline, 94.0 g. triethylamine and 420 ml. dry acetone was refluxed for 4.5 hours. The reaction mixture was concentrated under reduced pressure to give a residual oil. The residual oil was dissolved in methylene chloride, washed with dilute hydrochloride acid and then with water. The methylene chloride solution was then extracted with 10% aqueous sodium hydroxide and water. The combined sodium hydroxide and water was washed with diethyl ether and then acidified with 3 N hydrochloric acid to afford the crude product as a gummy solid. The crude product was triturated with isopropanol to yield 2-acetyl-7-(3-chlorobenzeneaminosulfonyl)-1,2,3,4-tetrahydroisoquinoline with a melting point of 150°-2° C.

Preparation of 7-(3-Chlorobenzeneaminosulfonyl)-1,2,3,4-Tetrahydroquinoline, Hydrochloride A mixture of 43.3 g (0.118 mole) 2-acetyl-7-(3-chlorobenzeneaminosulfonyl)-1,2,3,4-tetrahydroisoquinoline, 575 ml. 3 N hydrochloric acid and 60 ml. n-butanol was refluxed for 3 hours. The mixture was concentrated under reduced pressure. The residue was treated with warm isopropanol to afford 7-(3-chlorobenzeneaminosulfonyl)-1,2,3,4-tetrahydroquinoline hydrochloride as an off-white solid with a melting point of 215°-17° C.

Preparation of
N,N′-Bis[7-(3-Chlorobenzeneaminosulfonyl)-1,2,3,4-Tetrahydroisoquinolyl]Disulfonylimide To 8.05 g. (0.038 mole) bis(chlorosulfonyl)imide in 150 ml., dry acetonitrile at −40° C. was added dropwise 11.4 g. (0.113 mole) dry triethylamine. The reaction mixture was warmed to 0° C. and 27.0 g. (0.075 mole) 7-(3-chlorobenzeneaminosulfonyl)-1,2,3,4-tetrahydroisoquinoline hydrochloride in 9.9 g. (0.098 mole) triethylamine and 200 ml. acetonitrile was added slowly. The resultant mixture was stirred at ambient temperature for about 16 hours. The reaction mixture was concentrated under reduced pressure at less than 35° C. The residue was partitioned between ethyl acetate and dilute hydrochloric acid. The ethyl acetate fraction was dried over anhydrous sodium sulfate and filtered. The filtrate was concentrated under reduced pressure to afford the crude product. The crude product was recrystallized from methanol to yield N,N′-bis[7-(3-chlorobenzeneaminosulfonyl)-1,2,3,4-tetrahydroisoquinolyl]disulfonylimide with a melting point of 184°–185.5° C.

| Analysis   | C     | H    | N    | S     |
|------------|-------|------|------|-------|
| Calculated | 45.80 | 3.71 | 8.90 | 16.30 |
| Found      | 45.75 | 3.80 | 8.95 | 16.29 |

Following the procedure of Example 1, the appropriate substituted tetrahydroisoquinolines were reacted with bis(chlorosulfonyl)imide to afford the compounds indicated in the following table. The appropriate substituted tetrahydroisoquinolines were prepared by reacting the appropriate aniline derivative with 2-acetyl-7-chlorosulfonyl-1,2,3,4,-tetrahydroisoquinoline followed by deacylation.

EXAMPLE 2

Preparation of
2-Acetyl-7-Chloro-6-Chlorosulfonyl-1,2,3,4-Tetrahydroisoquinoline A solution of 2.0 g. (0.01 mole) 2-acetyl-7-chloro-1,2,3,4-tetrahydroisoquinoline in 15 ml. dry chloroform is added dropwise to 20 ml. chlorosulfonic acid at ambient temperature. The reaction mixture is stirred at ambient temperature for 24 hours and then refluxed at 60° C. for 2 hours. The reaction mixture is then cooled, poured onto a liter of ice and extracted with methylene chloride. The organic phase is dried over anhydrous magnesium sulfate, filtered and the filtrate is concentrated to dryness under reduced pressure to yield the desired product.

Preparation of
2-Acetyl-7-Chloro-6-(3-Chlorobenzeneaminosulfonyl)-1,2,3,4-Tetrahydroisoquinoline A mixture of 1.5 g. (1.6 mole) 2-acetyl-7-chloro-6-chlorosulfonyl-1,2,3,4-tetrahydroisoquinoline, 0.21 g. (1.6 mmole) 3-chloroaniline, a few drops of pyridine and 5 ml. dry acetone is heated at reflux for 16 hours. The reaction mixture is concentrated under reduced pressure to afford an oil residue, which is then dissolved in methylene chloride. The organic solution is washed with water, dilute hydrochloric acid and water. The organic solution is then extracted with 10% aqueous sodium hydroxide and water. The combined sodium hydroxide and water is then washed with diethyl ether and then acidified with 3 N hydrochloric acid to afford the crude product. The crude product is dissolved in methylene chloride, dried over anhydrous magnesium sulfate and filtered. The filtrate is concentrated to dryness under reduced pressure to afford the desired product.

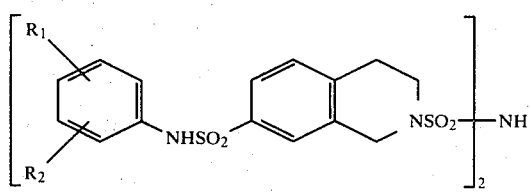

| Cmpd. No. | R | $R_1$ | $R_2$ | m.p. °C. | Calculated C | H | N | S | Halo | Found C | H | N | S | Halo |
|---|---|---|---|---|---|---|---|---|---|---|---|---|---|---|
| 2 | H | H | H | 179–182 | 50.20 | 4.35 | 9.76 | 17.86 | | 50.57 | 4.37 | 9.71 | 17.68 | |
| 3 | H | 2-Cl | H | 114 | 45.80 | 3.71 | 8.90 | 16.30 | | 45.41 | 3.64 | 8.95 | 16.16 | |
| 4 | H | 4-Cl | H | 198–200.5 | 45.80 | 3.71 | 8.90 | 16.30 | | 45.68 | 4.09 | 8.59 | 16.08 | |
| 5 | H | 3-Br | H | 180–182 | 41.15 | 3.34 | 8.00 | 14.64 | | 41.55 | 3.39 | 8.36 | 14.49 | |
| 6 | H | 4-Br | H | 205–208 | 41.15 | 3.34 | 8.00 | 14.64 | | 41.45 | 3.14 | 7.97 | 14.61 | |
| 7* | H | 3-$CF_3$ | H | 167–168 | 43.63 | 3.66 | 7.95 | 14.56 | | 43.99 | 4.02 | 7.47 | 14.19 | |
| 8 | H | 4-$CF_3$ | H | 213–215 | 45.01 | 3.42 | 8.20 | 15.02 | | 45.10 | 3.62 | 7.89 | 15.30 | |
| 9 | H | 3-$NO_2$ | H | 206–208 | 44.60 | 3.62 | 12.14 | 15.88 | | 44.48 | 3.73 | 12.00 | 16.05 | |
| 10 | H | 4-$OCH_3$ | H | 193–200.5 | 49.41 | 4.53 | 9.00 | 16.48 | | 49.64 | 4.72 | 8.85 | 16.35 | |
| 11 | H | 4-Cl | 3-Cl | 173–175 | 42.11 | 3.42 | 8.18 | 14.99 | 16.57 | 42.17 | 3.30 | 8.05 | 14.69 | 16.86 |
| 12 | H | 3-$CF_3$ | 4-Cl | 124.5–125 | 41.65 | 2.95 | 7.59 | 13.90 | | 41.65 | 3.15 | 7.57 | 14.10 | |
| 13 | H | 4-$CH_3$ | 3-$CH_3$ | 190.5–193.5 | 52.76 | 5.08 | 9.05 | 16.57 | | 52.80 | 5.33 | 8.69 | 16.39 | |
| 14 | H | 4-$CH_3$ | 3-Cl | 192.5–193.5 | 47.17 | 4.08 | 8.59 | 15.74 | 8.70 | 47.42 | 4.10 | 8.61 | 15.83 | 8.47 |
| 15 | $CH_3$ | 4-Cl | H | 206–209 | 47.17 | 4.08 | 8.59 | 15.74 | | 47.08 | 4.09 | 8.35 | 15.55 | |

*+1½ mole of $H_2O$

Preparation of N,N'-Bis[7-Chloro-6-(3-Chlorobenzeneamino sulfonyl)-1,2,3,4-Tetrahydroisoquinolyl]disulfonylimide 2-Acetyl-7-chloro-6-(3-chlorobenzeneaminosulfonyl)-1,2,3,4-tetrahydroisoquinoline is converted into N,N'-bis-[7-chloro-6-(3-chlorobenzeneaminosulfonyl)-1,2,3,4-tetrahydroisoquinolyl]disulfonylimide following the procedures described above in Example 1.

Additionally, compounds of the formula (III) which may be prepared employing analogous reactions are tabulated below:

| COMPOUND NUMBER | R | $R_1$ | $R_2$ | $X_2$ |
|---|---|---|---|---|
| 17 | H | H | H | 7-Br |
| 18 | H | 3-Br | H | 7-Br |
| 19 | H | 4-$CH_3$ | 3-$CH_3$ | 7-Cl |
| 20 | $CH_3$ | 4-Cl | H | 7-Cl |
| 21 | H | 4-$CH_3$ | 3-Cl | 7-Cl |
| 22 | H | 3-Br | H | 7-Cl |

EXAMPLE 3

Preparation of 2-Acetyl-7-Chloro-8-Chlorosulfonyl-1,2,3,4-Tetrahydroisoquinoline To a suspension of 16.0 g. (0.32 mole) sodium hydride (50% oil dispersion washed with hexane) and 250 ml. dry dimethylformamide under a blanket of Argon gas was added dropwise 50 ml. (0.43 mole) benzyl mercaptan in 100 ml. dry dimethylformamide at ambient temperature. After the evolution of hydrogen ceased, 24.5 g. (0.1 mole) 2-acetyl-7,8-dichloro-1,2,3,4-tetrahydroisoquinoline in 100 ml. dry dimethylformamide was added dropwise at ambient temperature. After 6 hours, the reaction mixture was cooled and then neutralized with concentrated hydrochloric acid. The dimethylformamide was removed under reduced pressure and the residue treated with 300 ml. water. After the pH of the aqueous residue was adjusted to 9 with 10% sodium hydroxide, it was extracted with ethyl acetate (3×100 ml.). The aqueous phase was then acidified with concentrated hydrochloric acid to give a crude white solid. This solid was dissolved in ethyl acetate, dried over anhydrous sodium sulfate and yield a yellowish-white solid with a melting point of 95°–111° C. The yellowish-white solid was then dissolved in 100 ml. glacial acetic acid and 30 ml. water. The reaction mixture was cooled with stirring to 15° C. and chlorine gas was bubbled through the reaction mixture for 1½ hours. To the reaction mixture was then added 100 ml. methylene chloride followed by 10 g. sodium bisulfite in 100 ml. water. The organic phase was collected and the aqueous phase extracted with methylene chloride (2×50 ml.). The combined organic phase was neutralized with a solution of sodium bicarbonate and solid sodium carbonate. The organic phase was collected and the aqueous phase extracted with methylene chloride (2×50 ml.). The combined organic phase was dried over anhydrous sodium sulfate, filtered and the filtrate concentrated to dryness to afford the desired product as a white solid with a melting point of 121°–125° C.

Preparation of 2-Acetyl-7-Chloro-8-(3-Chlorobenzeneaminosulfonyl)-1,2,3,4-Tetrahydroisoquinoline A mixture of 11.0 g. (0.036 mole) 2-acetyl-7-chloro-8-chlorosulfonyl-1,2,3,4-tetrahydroisoquinoline, 6.3 g. (0.05 mole) 3-chloroaniline, 8 ml. pyridine and 65 ml. acetone was converted into 2-acetyl-7-chloro-8-(3-chlorobenzeneaminosulfonyl)-1,2,3,4-tetrahydroisoquinoline as yellowish-white solid with a melting point of 193°–195° C. according to an analogous procedure employed in Example 4.

Preparation of N,N'-Bis[7-Chloro-8-(3-Chlorobenzeneaminosulfonyl)-1,2,3,4-Tetrahydroisoquinolyl]disulfonylimide 2-Acetyl-7-chloro-8-(3-chlorobenzeneaminosulfonyl)-1,2,3,4-tetrahydroisoquinoline was converted into N,N'-bis[7-cloro-8-(3-chlorobenzeneaminosulfonyl)-1,2,3,4-tetrahydroisoquinolyl]disulfonylimide following the procedures described in Example 1. The product so obtained was a white solid with a melting point of 177.5°–180° C.

| Analysis | C | H | N | S | Cl |
|---|---|---|---|---|---|
| Calculated | 42.11 | 3.18 | 8.18 | 14.99 | 16.57 |
| Found | 42.01 | 3.08 | 8.30 | 15.02 | 16.26 |

Additionally, compounds of the formula (IV) which may be prepared by employing analogous reactions are tabulated below:

| COMPOUND NUMBER | R | $R_1$ | $R_2$ | $X_3$ |
|---|---|---|---|---|
| 24 | H | H | H | H |
| 25 | H | 3-Br | H | 7-Br |
| 26 | $CH_3$ | 4-Cl | H | 7-Cl |
| 27 | H | 4-$CH_3$ | 3-$CH_3$ | H |
| 28 | H | 4-$CH_3$ | 3-Cl | 7-Cl |
| 29 | H | 3-Br | H | 7-Cl |

EXAMPLE 4

Preparation of 2-Acetyl-8-Chloro-1,2,3,4-Tetrahydroisoquinoline

A mixture of 20.4 g. (0.1 mole) 8-chloro-1,2,3,4-tetrahydroisoquinoline, hydrochloride, 9.85 g. (0.12 mole) sodium acetate 40 ml. acetic anhydride and 100 ml. acetic acid was heated for 3 hours on a steambath with stirring. After the solvent was removed under reduced pressure, the residue was dissolved in water which was then made basic with concentrated ammonium hydroxide. The crude product was extracted into methylene chloride and the organic solution was washed with water, 10% hydrochloric acid, water and 5% aqueous sodium bicarbonate. The organic solution was then dried over anhydrous magnesium sulfate and then concentrated to dryness under vacuum to afford 2-acetyl-8-chloro-1,2,3,4-tetrahydroisoquinoline as a yellow oil.

Preparation of 2-Acetyl-8-Chloro-5-Chlorosulfonyl-1,2,3,4-Tetrahydroisoquinoline 51.75 ml. (0.78 mole) of chlorosulfonic acid was added dropwise with stirring to a solution of 20.7 g. (0.099 mole) 2-acetyl-8-chloro-1,2,3,4-tetrahydroisoquinoline in 25 ml. of methylene chloride at −70° C. To effectuate a solution of the reactants 10 ml. of dry chloroform was added and the reaction mixture stirred for one hour at −70° C. The reaction mixture was then refluxed at 40°–45° C. for 2 hours and then stirred at ambient temperature for about 16 hours. The reaction mixture was then cautiously poured onto one liter of ice. The crude reaction product was then extracted into methylene chloride (3×100 ml.), washed with saturated sodium chloride solution, dried over anhydrous sodium sulfate and filtered. The filtrate was concentrated to dryness at reduced pressure to afford 2-acetyl-8-chloro-5-chlorosulfonyl-1,2,3,4-tetrahydroisoquinoline as whitish yellow solid with a melting point of 105°–115° C.

Preparation of
2-Acetyl-8-Chloro-5-(3-Chlorobenzeneaminosulfonyl)-1,2,3,4-Tetrahydroisoquinoline A mixture of 24.0 g. (0.078 mole) 2-acetyl-8-chloro-5-chlorosulfonyl-1,2,3,4-tetrahydroisoquinoline, 12.7 g. (0.1 mole) 3-chloroaniline, 15 ml. dry pyridine and 110 ml. dry acetone was stirred at reflux for 3 hours. The reaction mixture was concentrated under reduced pressure to give a brown residue. The residue was dissolved in methylene chloride, washed with dilute hydrochloric acid and then with water. The methylene chloride solution was then extracted with 10% aqueous sodium hydroxide and water. The combined sodium hydroxide and water was washed with diethyl ether and then acidified with 3 N hydrochloric acid to afford a white solid. The white solid was dissolved in ethyl acetate and dried over anhydrous sodium sulfate and activated charcoal, filtered and the filtrate concentrated at reduced pressure to afford the crude product. The crude product was recrystallized from methanol to yield 2-acetyl-8-chloro-5-(3-chlorobenzeneaminosulfonyl)-1,2,3,4-tetrahydroisoquinoline as a white solid with a melting point of 185°–187° C.

Preparation of
N,N'-Bis[8-Chloro-5-(3-Chlorobenzeneaminosulfonyl)-1,2,3,4-Tetrahydroisoquinolyl]disulfonylimide 2-Acetyl-8-chloro-5-(3-chlorobenzeneaminosulfonyl)-1,2,3,4-tetrahydroisoquinoline was converted into N,N'-bis[8-chloro-5-(3-chlorobenzeneaminosulfonyl)-1,2,3,4-tetrahydroisoquinolyl]disulfonylimide following the procedures described above in Example 1. The product so obtained was a yellowish-white solid with a melting point of 213°–215° C.

| Analysis | C | H | N | S | Cl |
|---|---|---|---|---|---|
| Calculated | 42.11 | 3.18 | 8.18 | 14.99 | 16.57 |
| Found | 42.46 | 3.20 | 8.27 | 15.16 | 16.88 |

Additionally, compounds of the formula (V) which may be prepared by employing analogous reactions are tabulated below:

| COMPOUND NUMBER | R | $R_1$ | $R_2$ | $X_4$ |
|---|---|---|---|---|
| 31 | H | H | H | 8-Br |
| 32 | H | 3-Br | H | 8-Br |
| 33 | H | 4-$CH_3$ | 3-$CH_3$ | 8-Cl |
| 34 | $CH_3$ | 4-Cl | H | 8-Cl |
| 35 | H | 4-$CH_3$ | 3-Cl | 8-Cl |
| 36 | H | 3-Br | H | 8-Cl |

EXAMPLE 5

Preparation of the Sodium Salt of Compound 1

A solution of 350 mg. N,N'-bis[7-(3-chlorobenzeneaminosulfonyl)-1,2,3,4-tetrahydroisoquinolyl]disulfonylimide in 20 ml. of methanol was passed through an ion exchange column (IR 120–14.2 g. sulfonic acid type resin in the sodium form) and the column eluted with methanol. The eluant was concentrated to near dryness and the resultant material triturated with diethyl ether which after filtration under nitrogen afforded the desired salt with a melting point of 155°–160° C.

| Analysis | C | H | N |
|---|---|---|---|
| Calculated | 44.57 | 3.25 | 8.72 |
| Found | 44.66 | 3.49 | 8.66 |

Alternatively, the desired salt was prepared by treating 500 mg. compound 1 with 9 ml. 1.4 M sodium methoxide in methanol under nitrogen at room temperature.

Similarly, alkali metal salts of the compounds of the present invention may be prepared.

EXAMPLE 6

Preparation of
2-Acetyl-5-Chloro-7-Chlorosulfonyl-1,2,3,4-Tetrahydroisoquinoline A solution of 2-chloro-4-methoxyaniline in acetone is reacted with methyl acrylate under Meerwein reaction conditions to afford 2'-bromo(2-chloro-4-methoxyphenyl) methylpropionate which is debrominated using zinc powder in acetic acid. The resultant 2-chloro-4-methoxyphenyl methylpropionate is converted to 2-chloro-4-methoxyphenethylisocyanate by reacting the acid chloride derivative with sodium azide. The isocyanate is then cyclized to 5-chloro-7-methoxy-1,2,3,4-tetrahydro-1-isoquinolone which is then converted to the tetrahydroisoquinoline with diborane in tetrahydrofuran. The tetrahydroisoquinoline is acylated with acetic anhydride prior to the conversion of the methoxy group to a hydroxy group with boron tribromide in methylene chloride. The resultant hydroxytetrahydroisoquinoline is converted into the mercapto derivative via a rearrangement of a dimethylthiocarbamate derivative followed by basic hydrolysis with sodium hydroxide in methanol. The resultant mercaptotetrahydroisoquinoline is then bis-acylated with acetic anhydride and then the thioacetate selectively cleaved with sodium hydroxide. The mercaptotetrahydroisoquinoline is then converted into the desired chlorosulfonyl compound with chlorine in glacial acetic acid followed by an aqueous sodium bisulfite workup.

Similarly, 2-acetyl-6-chloro-5-chlorosulfonyl-1,2,3,4-tetrahydroisoquinoline, 2-acetyl-7-bromo-5-chlorosulfonyl-1,2,3,4-tetrahydroisoquinoline and 2-acetyl-5-methyl-6-chlorosulfonyl-1,2,3,4-tetrahydroisoquinoline may be prepared.

The above chlorosulfonyltetrahydroisoquinolines can be converted to compounds of the present invention employing the procedures of Example 1 and the appropriately substituted anilines.

EXAMPLE 7

Preparation of
2-Acetyl-8-Chloro-7-Chlorosulfonyl-1,2,3,4-Tetrahydroisoquinoline 7-Methoxyisoquinoline is chlorinated with chlorine in acetic acid to afford the 8-chloro derivative which is demethylated with 48% hydrobromic acid. The resultant 8-chloro-7-hydroisoquinoline is converted into the 7 mercapto derivative via a xanthate intermediate as described in Example 6. The resultant 8-chloro-7-mercaptoisoquinoline is converted to the tetrahydro derivative with diboranedimethylsulfide in methylene chloride. The mercaptotetrahydroisoquinoline is reacted with chlorine and worked up with sodium bisulfite to afford 2-acetyl-8-chloro-7-chlorosulfonyl-1,2,3,4-tetrahydroisoquinoline.

6-Chloro-8-methoxyisoquinoline and 8-chloro-6-methoxyisoquinoline, which may be prepared from the appropriately substituted anisaldehyde via the procedure of Pomeranz-Fritsch as described in U.S. Pat. No. 3,988,339, may be converted into chlorosulfonyl compounds as described above.

These chlorosulfonyl compounds may be converted into compounds of the present invention by employing the procedures of Example 1 and using the appropriately substituted anilines.

EXAMPLE 8

Preparation of 2-Acetyl-5-Chloro-8-Chlorosulfonyl-1,2,3,4-Tetrahydroisoquinoline 5-Aminoisoquinoline is reacted with hydrochloric acid, sodium nitrite and cuprous chloride to afford 5-chloroisoquinoline, which was then reduced with diborane in tetrahydrofuran. The resultant 5-chlorotetrahydroisoquinoline was then acetylated with acetic anhydride and chlorosulfonated with chlorosulfonic acid at low temperature, for example $-50°$ C., to afford the desired chlorosulfonyl tetrahydroisoquinoline.

This compound may be converted into compounds of the present invention by employing the procedures in Example 1 and using the appropriately substituted anilines.

EXAMPLE 9

As a specific embodiment of a composition of this invention, an active ingredient, such as N,N'-bis[7-(3-chlorobenzeneaminosulfonyl)-1,2,3,4-tetrahydroisoquinolyl]disulfonylimide, is dissolved in sterile water at a concentration of 0.5% and aerosolized from a nebulizer operating at an air flow adjusted to deliver the desired aerosolized weight of drug.

What is claimed is:

1. A compound of the formula (I)

(I)

in which X is hydrogen, methyl, bromo or chloro; and Y is a benzeneaminosulfonyl radical of the formula in which R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chlorc, methyl or trifluoromethyl and when $R_2$ is methyl, $R_1$ is methyl; or an alkali metal salt of said compound.

2. A compound according to claim 1 of the formula (II)

(II)

in which $X_1$ is hydrogen, methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl; or an alkali metal salt of said compound.

3. A compound according to claim 2 in which $X_1$ is hydrogen.

4. A compound according to claim 3, in which R and $R_2$ are each hydrogen and $R_1$ is hydrogen, 3- or 4-bromo, 2-, 3- or 4-chloro, 3-nitro, 3- or 4-trifluoromethyl or 4-methoxy.

5. A compound according to claim 3 in which R is hydrogen, $R_2$ is 3-chloro and $R_1$ is 4-chloro or 4-methyl.

6. A compound according to claim 3 which is N,N'-bis[7-(4-chloro-3-trifluoromethylbenzeneaminosulfonyl)-1,2,3,4-tetrahydroisoquinolyl]disulfonylimide or an alkali metal salt thereof.

7. A compound according to claim 3 which is N,N'-bis[7-(3,4-dimethylbenzeneaminosulfonyl)-1,2,3,4-tetrahydroisoquinolyl]disulfonylimide or an alkali metal salt thereof.

8. A compound according to claim 3 which is N,N'-bis[7-(3-chlorobenzeneaminosulfonyl)-1,2,3,4-tetrahydroisoquinolyl]disulfonylimide or an alkali metal salt thereof.

9. A compound according to claim 3 which is N,N'-bis[7-(3-bromobenzeneaminosulfonyl)-1,2,3,4-tetrahydroisoquinolyl]disulfonylimide or an alkali metal salt thereof.

10. A compound according to claim 3 which is N,N'-bis[7-(N-methyl-4-chlorobenzeneaminosulfonyl)-1,2,3,4-tetrahydroisoquinolyl]disulfonylimide or an alkali metal salt thereof.

11. A compound according to claim 3 which is N,N'-bis[7-(3-chloro-4-methylbenzeneaminosulfonyl)-1,2,3,4-tetrahydroisoquinolyl]disulfonylimide or an alkali metal salt thereof.

12. A compound according to claim 3 which is N,N'-bis[7-(3-trifluoromethylbenzeneaminosulfonyl)-1,2,3,4-tetrahydroisoquinolyl]disulfonylimide or an alkali metal salt thereof.

13. A compound according to claim 1 of the formula (III)

(III)

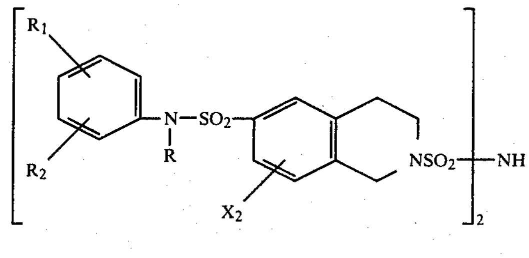

in which $X_2$ is methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt thereof.

14. A compound according to claim 1 of the formula (IV)

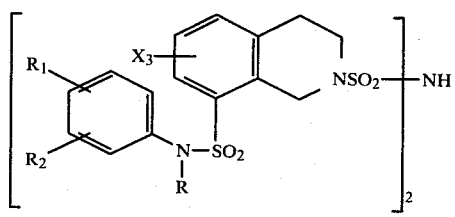

(IV)

in which $X_3$ is hydrogen, methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt thereof.

15. A compound according to claim 14 which is N,N'-bis[7-chloro-8-(3-chlorobenzeneaminosulfonyl)-1,2,3,4-tetrahydroisoquinolyl]disulfonylimide or an alkali metal salt thereof.

16. A compound according to claim 1 of the formula (V)

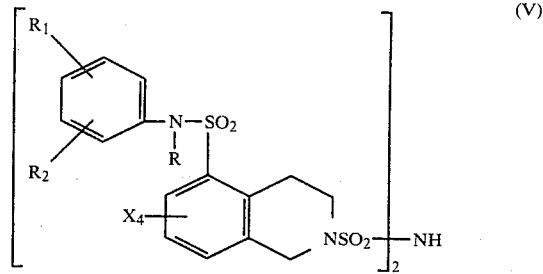

(V)

in which $X_4$ is methyl, bromo or chloro; R is hydrogen or methyl; $R_1$ is hydrogen, bromo, chloro, nitro, methyl, trifluoromethyl or methoxy; and $R_2$ is hydrogen, chloro or methyl provided that when $R_2$ is chloro, $R_1$ is chloro, methyl or trifluoromethyl and when $R_2$ is methyl, $R_1$ is methyl or an alkali metal salt thereof.

17. A compound according to claim 16 which is N,N'-bis[8-chloro-5-(3-chlorobenzeneaminosulfonyl)-1,2,3,4-tetrahydroisoquinolyl]disulfonylimide or an alkali metal salt thereof.

18. A pharmaceutical composition for inhibiting the symptoms of asthma comprising a pharmaceutical carrier or diluent and an amount sufficient to produce said inhibition of a compound of claim 1.

19. A pharmaceutical composition according to claim 18 in a form suitable for administration by inhalation.

20. A pharmaceutical composition according to claim 18 comprising a solution or suspension of the active ingredient in sterile water.

21. A pharmaceutical composition according to claim 18 in the form of an aerosol formulation.

22. A pharmaceutical composition according to claim 18 in which the pharmaceutical carrier or diluent is a solid.

23. A method of inhibiting the symptoms of asthma which comprises administering to a subject in need of said inhibition a therapeutically effective amount for producing said inhibition of a compound of claim 1.

24. The method according to claim 23 in which the active ingredient is administered in a daily dosage regimen of from about 0.5 mg. to about 2000 mg.

25. A method of antagonizing the effects of SRS-A on bronchial smooth muscle which comprises administering to a subject in need of said antagonism an amount sufficient to produce said antagonism of a compound of claim 1.

* * * * *